(12) United States Patent
Yi

(10) Patent No.: US 11,666,554 B2
(45) Date of Patent: Jun. 6, 2023

(54) USE OF A CARBAMATE COMPOUND TO PREVENT, ALLEVIATE OR TREAT VISCERALGIA OR PAIN ARISING FROM VISCERAL DISEASE

(71) Applicant: SK BIOPHARMACEUTICALS CO., LTD., Gyeonggi-do (KR)

(72) Inventor: Han Ju Yi, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 0 days.

(21) Appl. No.: 16/763,751

(22) PCT Filed: Nov. 13, 2018

(86) PCT No.: PCT/KR2018/013768
§ 371 (c)(1),
(2) Date: May 13, 2020

(87) PCT Pub. No.: WO2019/098633
PCT Pub. Date: May 23, 2019

(65) Prior Publication Data
US 2020/0368203 A1 Nov. 26, 2020

(30) Foreign Application Priority Data
Nov. 14, 2017 (KR) .......................... 10-2017-0151256

(51) Int. Cl.
*A61K 31/41* (2006.01)
*A61P 29/00* (2006.01)

(52) U.S. Cl.
CPC .............. *A61K 31/41* (2013.01); *A61P 29/00* (2018.01)

(58) Field of Classification Search
CPC ........... A61K 31/41; A61P 25/04; A61P 29/00
USPC ....................................................... 514/381
See application file for complete search history.

(56) References Cited

U.S. PATENT DOCUMENTS 7,598,279 B2 * 10/2009 Choi .................... C07D 257/04
514/359
10,849,882 B2 * 12/2020 Jo .......................... A61P 29/00

2010/0144767 A1 6/2010 Fisher et al.
2012/0004211 A1 1/2012 Jagerovic et al.
2017/0029382 A1 2/2017 Bosmans et al.

FOREIGN PATENT DOCUMENTS

| KR | 10-1286499 B1 | 7/2013 |
| KR | 10-2019-0054559 A | 5/2019 |
| WO | WO-2006-048771 A1 | 5/2006 |
| WO | WO-2006-112685 A1 | 10/2006 |
| WO | WO-201 0-150946 A1 | 12/2010 |
| WO | WO-2011-046380 A2 | 4/2011 |

OTHER PUBLICATIONS

Bialer, et al. (2015) Progress reporton new antiepileptic drugs: A summary of the Twelfth Eilat Conference (EILAT XII). Epilepsy Research, 111:85-141.
Qi, et al. (2011) "Targeting voltage-gated sodium channels for treatment for chronic visceral pain." *World J Gastroenterol*, May 21, 2011, 17(19):2357-2364.
International Search Report issued in International Patent Application No. PCT/KR2018/013768, dated Feb. 19, 2019, with English Translation.
Ness, T.J. (1999) "Models ofVisceral Nociception." *ILAR Journal*, 40(3):119-128.
Extended European Search Report from corresponding European Patent Application No. 18878130.6, dated Oct. 20, 2021.
Bialer, M., et al.; Progress report on new antiepileptic drugs: A summary of the Eleventh Eilat Conference (EILAT XI):, Epilepsy Research, 2013,103, pp. 2-30.
Stepanovic-Petrovic, R. M., et al.; "The Antinociceptive Effects of Anticonvulsants in a Mouse Visceral Pain Model", Anesthesia and Analgesia, vol. 106, No. 6, Jun. 2008, pp. 1897-1903.
Knowles, C. H., et al.: "Basic and clinical aspects of gastrointestinal pain", Pain 141, 2009, pp. 191-209.

* cited by examiner

*Primary Examiner* — Charanjit Aulakh

(74) *Attorney, Agent, or Firm* — Harness, Dickey & Pierce, P.L.C.

(57) ABSTRACT

The present invention relates to use of a carbonate compound of chemical formula 1, or a pharmaceutically permissible salt, solvate or hydrate thereof, for prevention, alleviation or treatment of visceralgia, or pain arising from visceral disease.

7 Claims, No Drawings

USE OF A CARBAMATE COMPOUND TO PREVENT, ALLEVIATE OR TREAT VISCERALGIA OR PAIN ARISING FROM VISCERAL DISEASE

CROSS-REFERENCE TO RELATED APPLICATIONS

This application is a national phase application of PCT Application No. PCT/KR2018/013768, filed on Nov. 13, 2018, which claims priority to Korean Patent Application No. 10-2017-0151256, filed on Nov. 14, 2017. The entire disclosure of the applications identified in this paragraph is incorporated herein by reference.

FIELD

The present invention relates to use of a carbamate compound of the following Formula 1, or a pharmaceutically acceptable salt, solvate or hydrate thereof for preventing, alleviating or treating visceral pain or pain caused by visceral diseases:

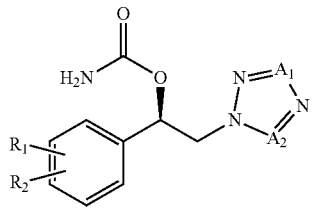

[Formula 1]

wherein,
$R_1$, $R_2$, $A_1$ and $A_2$ are as defined herein.

BACKGROUND

Pain is defined as an unpleasant sensory and emotional experience associated with actual or potential tissue damage (International Association for the study of Pain, 1980).

In general, pain is divided into nociceptive, inflammatory, neuropathic and functional pain. Among them, nociceptive pain refers to pain which is caused by the normal pain transmission path being activated by harmful stimuli such as mechanical, chemical and temperature applied to the peripheral nociceptors that detect pain, and this is further divided into somatic pain and visceral pain.

Somatic pain is a pain in the skin, muscles and bones, and the pain area is limited to a specific area. Somatic pain appears as a sharp, throbbing or pressing pattern. However, in the case of visceral pain, it is a pain that occurs from internal organs such as the abdomen or rib cage due to the expansion or extension and inflammation of the internal organs of the human body, and thus shows characteristic of being difficult to know the exact pain area. This is because nociceptors of internal organs—such as the stomach and small intestine—are only about one-fiftieth of the skin. Therefore, the internal organs with sparse nociceptors are painful only when the irritation of a wide area is felt, so it is impossible to pinpoint the painful area. For example, in the case of the digestive system, when a large area is stimulated by a large amount of food or excess stomach acid, it may feel nociceptive, but it does not feel nociceptive by local irritation such as pricking with a needle or cutting with scissors. In addition, there are parts of the internal organs that do not feel nociceptive. For example, there are nociceptors in the stomach, small intestine and heart, but there are no nociceptors in the liver, lungs and kidneys, so there is no pain even when a disease occurs. In the case of lung cancer or liver cancer, this is why the prognosis is poor by it not being found at an early stage. These visceral pains are observed as the abdomen constantly tightens or throbs, and are often accompanied by autonomic nervous system symptoms such as discomfort, nausea, vomiting, sweating and bradycardia.

In addition, all internal organ sensations that occur in the internal organs are transported to the brainstem and visceral body cortex via the vagus nerve through the inferior ganglion, the primary sympathetic afferent nerve through the dorsal root ganglion (DRG) and the secondary nerve cells of the dorsal horn. However, because there are no nerve cells responsible for only visceral pain, nerve cells that deliver somatic pain transmit the visceral pain together. For this reason, the visceral pain sometimes shows referred pain accompanied by dermalgia which is somatic pain. Examples of referred pain are as follows: pain caused by angina pectoris spreads to the chest, arms and hands; pain in the gallbladder spreads to the shoulders; pain in the esophagus spreads to the chest wall; pain in the ureter spreads to the lower abdomen; bladder pain spreads to the perineum; and abdominal pain due to appendicitis is enlarged to the abdominal wall around the navel. Therefore, if referred pain is closely observed, visceral pain can be more accurately diagnosed.

The causes of visceral pain include various visceral diseases such as tumors, inflammation, ischemic and mechanical obstruction. In general, visceral pain refers to pain in the digestive organs such as the respiratory tract, stomach and pancreas, and urinary/reproductive organs, but may also include cancer pain caused by tumor invasion to the organ membrane. In addition, as in the case of cystitis or reflux esophagitis, it may be closely related to inflammation. However, visceral pain is not always associated with visceral disease, and sometimes it may be caused by other non-intestinal factors. They often develop pain due to complex nervous system action, and may persist even though the cause of visceral pain has been entirely or partially eliminated.

Visceral pain has been associated with various diseases. In addition to visceral pain resulting from diseases of the digestive system including gastritis, duodenitis or colitis, cholecystitis, pancreatitis, appendicitis, Crohn's disease, irritable bowel syndrome, non-ulcerative dyspepsia, it also includes postpartum pain, serious menstrual pain or abdominal pain due to menstrual irregularity, pain after abdominal surgery related to intestinal obstruction, epigastric pain, pleural pain, substernal pain caused by initial myocardial infarction.

There is a continually increasing need to develop analgesics suitable for effective treatment of visceral pain. Specifically, narcotic analgesics such as morphine are still being used to alleviate severe visceral pain of organic diseases such as visceral cancer. However, the use of narcotic analgesics—in addition to the analgesic effect—causes various side effects such as hypopnea, nausea, vomiting, dizziness, mental turbidity, discomfort, itching, constipation, increased biliary pressure, urinary tract obstruction, hypotension and sedation. Especially, there is a major concern about the side effect of addiction such as physical dependency. In addition, there is a phenomenon in which the drug efficacy is lowered due to drug tolerance caused by repeated use.

Therefore, in the treatment of visceral pain or pain caused by visceral diseases, there is a growing need for developing a new non-opioid analgesic that can alleviate pain with high efficiency while reducing the possibility of unwanted effects. At the same time, there is a need for developing an analgesic that can suppress pain with high efficiency even at a low dosage in order to avoid or at least reduce adverse side effects observed at high dosages.

SUMMARY

Problem to be Solved

The present invention is intended to provide a method for the prevention, alleviation or treatment of visceral pain or pain caused by visceral diseases.

The present invention is also intended to provide the use of a therapeutically effective amount of a carbamate compound of the following Formula 1, or a pharmaceutically acceptable salt, solvate or hydrate thereof, for the prevention, alleviation or treatment of visceral pain or pain caused by visceral diseases:

[Formula 1]

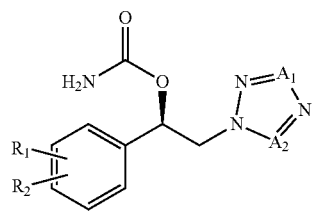

wherein,
$R_1$, $R_2$, $A_1$ and $A_2$ are as defined herein.

Technical Solution to the Problem

The present invention provides a medicament for the prevention, alleviation or treatment of visceral pain or pain caused by visceral diseases, comprising a therapeutically effective amount of a carbamate compound of the following Formula 1, or a pharmaceutically acceptable salt, solvate or hydrate thereof:

[Formula 1]

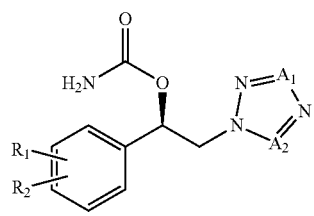

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

In addition, the present invention provides a pharmaceutical composition for the prevention, alleviation or treatment of visceral pain or pain caused by visceral diseases, comprising a therapeutically effective amount of the carbamate compound of the above Formula 1, or a pharmaceutically acceptable salt, solvate or hydrate thereof, and further one or more of a pharmaceutically acceptable carrier.

In addition, the present invention provides a method for preventing, alleviating or treating visceral pain or pain caused by visceral diseases, in a subject, comprising administering to the subject a therapeutically effective amount of the carbamate compound of the above Formula 1, or a pharmaceutically acceptable salt, solvate or hydrate thereof.

In addition, the present invention provides the use of the carbamate compound of the above Formula 1, or a pharmaceutically acceptable salt, solvate or hydrate thereof for the prevention, alleviation or treatment of visceral pain or pain caused by visceral diseases.

According to one embodiment of the present invention, in the above Formula 1, $R_1$ and $R_2$ are each independently selected from the group consisting of hydrogen, halogen and $C_1$-$C_8$ alkyl.

In one embodiment of the present invention, the halo-$C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

[Formula 2]

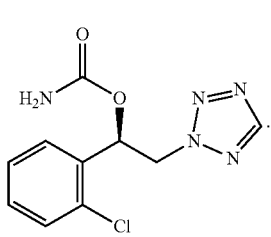

A person having ordinary skill in the art of synthesis of compounds could have easily prepared the carbamate compounds of the above Formulas 1 and 2 using known compounds or compounds which can be easily prepared therefrom. Specifically, methods for preparing the compounds of the above Formula 1 are described in detail in International Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of visceral pain or pain caused by visceral diseases, and symptoms associated therewith.

According to another embodiment of the present invention, in visceral pain or pain caused by visceral diseases, the visceral diseases include various diseases related to internal organs caused by tumors, inflammation, ischemia, and mechanical obstruction.

According to another embodiment of the present invention, the visceral pain or pain caused by visceral diseases may be, but is not limited to, pain caused by cholecystitis, cholangitis, pancreatitis, pneumonia, pneumothorax, pleurisy, pleural pain, diaphragmatic abscess, hepatitis, Budd-Chiari syndrome, splenic infarction, splenic rupture, spleen abscess, gastritis, gastric ulcer, appendicitis, salpingitis, oophoritis, inguinal hernia, ectopic pregnancy, kidney stones, nephritis, cystitis, inflammatory colitis, mesenteric lymphadenitis, diverticulitis, irritable bowel syndrome, Crohn's disease, digestive ulcers, non-ulcerative dyspepsia, gastroesophageal reflux disease, abdominal aortic aneurysm rupture, abdominal aortic dissection, angina, myocardial infarction, myocarditis, endocarditis, esophagitis, pulmonary embolism, other heart and lung diseases, gastroenteritis, intestinal obstruction, aortic aneurysm rupture, peritonitis, very severe hyperlipidemia, hyperparathyroidism, acute adrenal insufficiency, porphyria, lead poisoning, heat stroke, shingles, visceral membrane tumors, childbirth, severe menstruation, and the like.

According to another embodiment of the present invention, the visceral pain or pain caused by visceral diseases may be acute or chronic, and may be mild or severe pain.

In addition, as types of visceral pain, true or localized visceral pain, referred visceral pain, localized parietal pain, and referred parietal pain have been known.

As a representative animal experimental model widely used to confirm the analgesic effect on visceral pain, an acetic acid-induced writhing test is used [T. J. Ness, Models of Visceral Nociception (1999) ILAR Journal 40: 119-128]. At this time, acetic acid is a chemical that is a stimulus used to induce pain, and when it is injected into the abdominal cavity of the mouse, characteristic writhing pain behaviors are induced in which due to the inflammatory pain caused in the peritoneum the mouse stretches both the forelimbs and the hind legs, and touches the abdomen to the floor or twists. However, when a drug having an analgesic effect, such as morphine, is injected into a mouse, the writhing pain behaviors of the mouse is reduced. As such, the degree of decreasing the writhing pain behaviors is measured to confirm the analgesic effect of the drug.

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above. The therapeutically effective amount of the compound of Formula 1 is 50 to 500 mg, 50 to 400 mg, 50 to 300 mg, 100 to 400 mg, 100 to 300 mg, 50 to 200 mg, or 100 to 200 mg, based on the free form and once-daily administration to humans.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbam ate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated as a plain tablet (uncoated tablet) or such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, colloidal silicon dioxide.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat visceral pain or pain caused by visceral diseases.

DETAILED DESCRIPTION

Hereinafter, the present invention will be explained in more detail through working examples. However, the following working examples are only intended to illustrate one or more embodiments and are not intended to limit the scope of the invention.

PREPARATION EXAMPLE

Synthesis of Carbamic acid (R)-1-(2-chlorophenyl)-2-tetrazol-2-yl-ethyl ester

Carbamic acid (R)-1-(2-chlorophenyl)-2-tetrazol-2-yl-ethyl ester (hereinafter referred to as "Test Compound") was prepared according to the method described in Preparation Example 50 of International Publication No. WO 2010/150946.

EXAMPLE

Analgesic Effect in Acetic Acid-Induced Writhing Test

Experimental Animals

Male ICR mice (body weight: 24 to 30 g) were used in this experiment. The experimental animals were maintained at a light-and-darkness cycle of 12 hours, a temperature of 22 to 25° C., a relative humidity of 40 to 60%, and free access to water and food. For stabilization of animal behavior, the experimental animals were allowed to acclimate to the laboratory conditions for at least 1 hour before the test.

Drug Administration, Acetic Acid Injection and Measurement of Pain Behavior

As a vehicle serving as the negative control, 30% PEG400 (v/v) was used, and Test Compound was dissolved in the vehicle and administered orally at doses of 3, 10 and 30 mg/kg. Morphine which is the positive control was dissolved in saline and administered subcutaneously at a dose of 10 mg/kg. The final dose of solution was 10 ml/kg.

After 1 hour of oral administration of the vehicle and Test Compound or 30 minutes after subcutaneous administration of morphine, the mice were gently restrained, and 0.8% (v/v) acetic acid solution was administered intraperitoneally to the abdomen of the mice. The mice were immediately returned to the observation box, and the number of writhing pain behaviors of the mice for 10 minutes was recorded.

Statistics

The effect of the compound was expressed as the mean±standard error, and statistical significance was recognized when data differed by $p<0.05$ using one-way ANOVA and Dunnett's test.

Experiment Result

As can be seen from Table 1, when Test Compound was administered orally, a statistically significant decrease in pain behavior was observed compared to the vehicle administration group. This reduction in pain behavior was observed in a dose-dependent manner, showing a pain suppression rate of 25.8% in the 3 mg/kg group, 66.1% in the 10 mg/kg group and a perfect pain suppression rate of 100% in the 30 mg/kg group. In addition, in the positive control (morphine) group, a significant reduction in pain behavior of 98.2% was observed by subcutaneous administration of 10 mg/kg.

TABLE 1

Acetic acid-induced writhing test

| Treatment drug | Dosage (mg/kg, p.o.) | Number of animals | Number of writhing (writes/10 minutes) | Suppression rate compared to negative control[2] |
|---|---|---|---|---|
| Vehicle | 0 | 8 | 23.3 ± 1.9 | — |
| Morphine | 10 (s.c) | 7 | 0.4 ± 0.3[1] | 98.2% |
| Test Compound | 3 | 8 | 17.3 ± 2.6 | 25.8% |
|  | 10 | 8 | 7.9 ± 2.4[1] | 66.1% |
|  | 30 | 8 | 0.0 ± 0.0[1] | 100.0% |

[1] Significance of pain behavior time in comparison with negative; p < 0.01
[2] Suppression rate compared to negetive control = [(vehicle group average of writhing number − morphine or Test Compound group average)/vehicle group average of writhing number] × 100

From the above results of the pain model experiments, it was confirmed that

Test Compound has a significant effect on visceral pain or pain caused by visceral diseases. In addition, it was confirmed that Test Compound exhibits a pharmacological effect at a level comparable to the narcotic analgesic, morphine which has already been used as a therapeutic agent for patients suffering from visceral pain or pain caused by visceral diseases.

What is claimed is:

1. A method for alleviating or treating visceral pain or pain caused by visceral diseases in a subject, comprising administering a therapeutically effective amount of a carbamate compound of the following Formula 1, or a pharmaceutically acceptable salt, solvate or hydrate thereof to the subject:

[Formula 1]

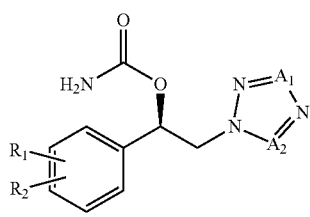

wherein, $R_1$ and R2 are each independently selected from the group consisting of hydrogen, halogen, and $C_1$-$C_8$ alkyl; and one of $A_1$ and $A_2$ is CH, and the other is N.

2. The method according to claim 1, wherein the carbamate compound of Formula 1 is carbamic acid (R)-1-(2-chlorophenyl)-2-tetrazol-2-yl-ethyl ester of the following Formula 2:

[Formula 2]

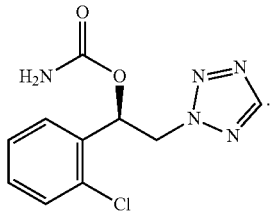

3. The method according to claim 1, wherein the visceral disease is a disease related to internal organs caused by tumors, inflammation, ischemia or mechanical obstruction.

4. The method according to claim 1, wherein the visceral pain or pain caused by visceral diseases is a pain caused by cholecystitis, cholangitis, pancreatitis, pneumonia, pneumothorax, pleurisy, pleural pain, diaphragmatic abscess, hepatitis, Budd-Chiari syndrome, splenic infarction, splenic rupture, spleen abscess, gastritis, gastric ulcer, appendicitis, salpingitis, oophoritis, inguinal hernia, ectopic pregnancy, kidney stones, nephritis, cystitis, inflammatory colitis, mesenteric lymphadenitis, diverticulitis, irritable bowel syndrome, Crohn's disease, digestive ulcers, non-ulcerative dyspepsia, gastroesophageal reflux disease, abdominal aortic aneurysm rupture, abdominal aortic dissection, angina, myocardial infarction, myocarditis, endocarditis, esophagitis, pulmonary embolism, other heart and lung diseases, gastroenteritis, intestinal obstruction, aortic aneurysm rupture, peritonitis, very severe hyperlipidemia, hyperparathyroidism, acute adrenal insufficiency, porphyria, lead poisoning, heat stroke, shingles, visceral membrane tumors, childbirth or severe menstruation.

5. The method according to claim 1, wherein the subject is a mammal.

6. The method according to claim 5, wherein the mammal is a human.

7. The method according to claim 1, wherein the therapeutically effective amount of the carbamate compound of Formula 1 is 50 to 500 mg based on the free form once-daily administration.

* * * * *